US00PP08650P

United States Patent [19]

Imazio

[11] Patent Number: Plant 8,650

[45] Date of Patent: Mar. 22, 1994

[54] HEATH PLANT NAMED HAPPY

[75] Inventor: Bruno L. Imazio, Watsonville, Calif.

[73] Assignee: Bay City Flower Co., Half Moon Bay, Calif.

[21] Appl. No.: 964,521

[22] Filed: Oct. 21, 1992

[51] Int. Cl.[5] ..... A01H 5/00

[52] U.S. Cl. ..... Plt./54.1

[58] Field of Search ..... Plt. 68.1, 54.1, 100

[56] References Cited

U.S. PATENT DOCUMENTS

Plt 7536 5/1991 Imazio ..... Plt./54.1

Plt 8014 10/1992 Imazio ..... Plt./54.1

*Primary Examiner*—James R. Feyrer

*Assistant Examiner*—Erich E. Veitenheimer

*Attorney, Agent, or Firm*—James R. Cypher

[57] ABSTRACT

The present invention relates to a new and distinct variety of heath plant named Erica persoluta 'Happy', a seedling on unknown pollen and seed parentage, discovered in a field of Erica persoluta, which is distinguished from Erica persoluta and other varieties known to me by its early flowering habit, dense and compact appearance, natural short growth habit, orchid colored blooms that cover the plume from the base of the stem all the way to the tip of the plant, and its tight, narrow and erect plumes spike-like flower clusters.

1 Drawing Sheet

BACKGROUND OF THE INVENTION

This invention relates to a new and distinct plant variety of the Ericaceae family which has been named *Erica persoluta* 'Happy' by the assignee of the invention. This new heather variety was discovered by the inventory as a seedling of unknown pollen and seed parentage growing in a cultivated field of *Erica persoluta.* The new variety was noticed because of its early flowering habit, dense and compact appearance, natural short growth habit, orchid colored blooms which bloom to the tip of the plant, and its tight, narrow and erect spike-like flower clusters.

The new variety is desirable for potted plant culture because of it natural compact, dwarfish growth habit which requires minimal pruning to achieve the abundant branching and full, dense appearance desired.

The distinguishing characteristics of my new variety which differentiate it from *Erica persoluta* and other varieties known to me are:

1. early bloom time of October through mid January,
2. short, dense, compact growth habit,
3. natural abundant branching with minimal pruning,
4. orchid colored blooms which bloom to the tip of the plant, and,
5. tight, narrow and erect spike-like flower clusters.

The distingushing characteristics of my new variety which differentiate it from *Erica persoluta,* 'Heidi' and 'Rosemarie' are bloom time and color blooms.

| | 'HAPPY' | 'HEIDI' | 'ROSEMARIE' | *ERICA PERSOLUTA* |
|---|---|---|---|---|
| Bloom Season | Oct.–Mid Jan. | Mid Dec.–Mid Feb. | Dec.–Feb. | March |
| Bloom Color | 78C–78D | 71C–71D | 66D | 70A–70B |

Since the inventor's discovery of the new plant, the assignee, under the direction and control of the inventor at Half Moon Bay, has asexually reproduced the new cultivar through successive generations by means of cuttings and has found that its following characteristics remain true from generation to generation and appear to be firmly fixed: early bloom time; shorter, dense, compact growth habit; natural abundant branching which requires minimal pruning; orchid colored blooms which bloom to the tip of the plant; and tight, thin and erect spike-like flower clusters.

DETAILED DESCRIPTION OF THE DRAWING

Figure 2:
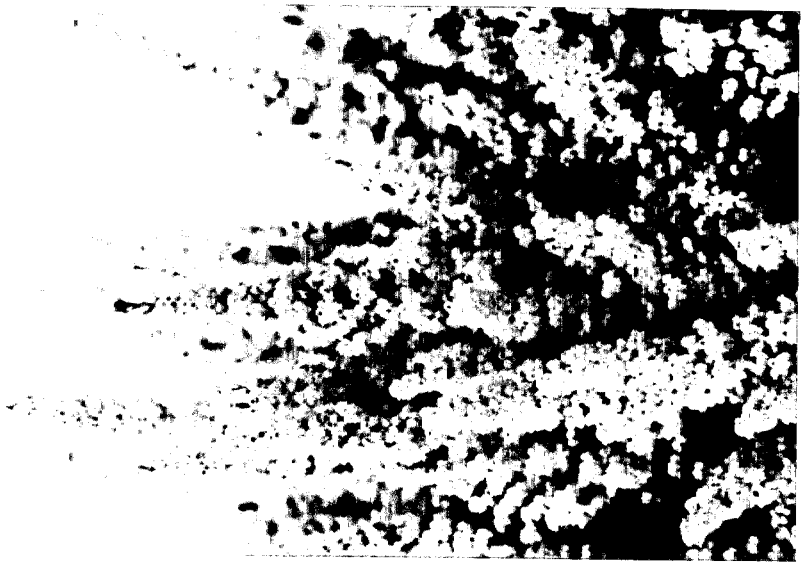
FIG. 2 is a close up view of the plumes of the new variety illustrating the abundance of blooms on the plumes and blooms all the way to the tip of the plant.
Figure 1:
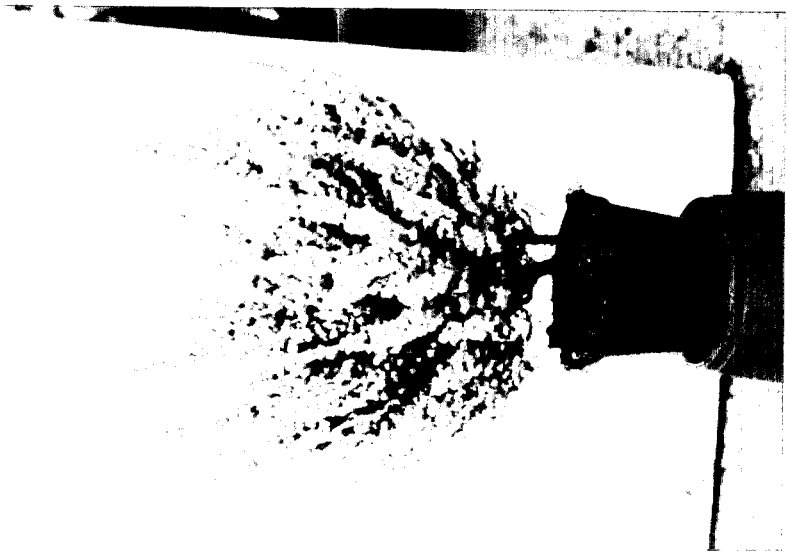
FIG. 1 is a color photograph of a potted plant of the new variety illustrating the overall appearance and form of the plant, including: abundant branching; short height; dense compact appearance; tight, narrow and erect plumes; and blooms all the way to the tip of the plant.

The following is a detailed description of the new variety with color designations according to the R.H.S. Colour Chart published by The Royal Horticultural Society of London, England. The following description is based on observations of well fertilized 4" potted plants of 12 to 16 months of age from initial propagation which were grown outside under saran in a commercial nursery at Half Moon Bay, Calif., where temperature average from 55 to 65 degrees F. during the summer months, and 45 to 55 degrees F. during the winter months.

Color designation and other values stated may deviate slightly from the slated values from flowering to flowering, but the deviations will be within the range expected from varying environmental, seasonal, and cultural conditions.

The Plant

Origin: Seedling.

Parentage:

*Seed parent.*—Unknown.

*Pollen parent.*—Unknown.

Classification:

*Botanic.*—*Erica persoluta* 'Happy'.

*Commercial.*—'Happy'.

Form: Perennial, compact, woody shrub.

Shape: Upright, stems curving slightly to accomodate fullness of plant.

Height: Mean 12" to 18".

Girth: Mean 8" to 10".

Branching: Ample, needs minimal pruning.

Growth: naturally compact with woody flexible strength.

Foliage: Abundant, with tiny needle-like leaves over the entire plant.

*Size of leaf.*—Mean ⅛" long.

*Shape of leaf.*—Acerose like.

*Character.*—Sulcate.

*Color.*—R.H.S. 144 A.

*Texture.*—Smooth.

Hardiness: Can tolerate a temperature range of 28 to 100 degrees F.

Disease resistance: Considerable resistance to fungus type diseases. Common diseases include phythium and phytoplhora.

Seed production: Sparce; commercially produced asexually by cuttings.

Effects of weather: Prolonged exposure to hot weather is detrimental to plant appearance. Extended periods of hot, sunny, dry weather will accelerate blooming and cause blooms to decline more quickly, shortening its lasting quality.

In general, the foliage is too tiny to determine further characteristics by plant observation.

The Bud

Size:

*Length.*—⅛" and less.

*Diameter.*—1/10"and less.

Rate of opening: progressive and continuous to the tip of the stem.

Petals: Corolline flowers in which the sepals are relatively insignificant.

Color: R.H.S. 78 B to 78 D.

Inflorescence

Blooming habit: Annually, can range from early October through mid January depending upon seasonal weather conditions.

Size of bloom: ⅛" by 1/10".

Borne: Spike like clusters with terminal flowers.

Shape: Urceolate.

Appearance: Satiny.

Color: R.H.S. 78 B to 78 C in overall appearance of the plant.

Flower stem:

*Length.*—Mean ¼" to 3".

*Color.*—R.H.S. 177D.

*Strength.*—Woody and supple.

Discoloration: Does not fade.

Effects of weather: Prolonged exposure to hot weather is detrimental to plant appearance. Extended periods of hot, dry, sunny weather will accelerate blooming and cause blooms to fade and decline more quickly, shortening its lasting quality.

Persistence: Blooms persists long after the stem ceases to draw water. Blooms do not shed easily.

Fragrance: Slight.

Lasting quality:

*On plant.*—6 to 8 weeks.

*As a cut flower.*—2 weeks.

The outstanding characteristics of this new plant resides in its early blooming from October through mid January, whereas Erica persoluta does not begin to bloom until March. Its natural short, compact growth habit makes it suitable for pot plant culture, whereas

*Erica persoluta* is of the cut flower variety and is taller.

| PLANT | 'HEIDI' | 'ROSE-MARIE' | '*ERICA PERSOLUTA*' | NEW CULTIVAR |
|---|---|---|---|---|
| Height | a 4" pot will be 8" or 9" high in 18 mons. growing time with little or no pruning | Same | a 4" pot will be 10" to 12" high in 18 mons. growing time with numerous pruning | a 4" pot will be 13" to 15" high in 16 mons. growing time with minimal pruning |
| Form | short, dense appearing, compact woody shrub | Same | Same | Same |
| Shape | Upright, stems curving slightly to accomodate fullness of plant | Same | Upright, stems spreading to produce fullness of plant | Upright, stems curving slightly to accommodate fullness of plant |
| Branch-ing | naturally generous, minimal or no pruning needed | Same | generous, several prunings necessary (4–5) to encourage branching | ample, minimal (1–2) prunings necessary to encourage branching |
| Growth | upright but naturally short and branching with woody, flexible strength | Same | Same | Same |
| Blooming Season: | annual, mid Jan. to mid Feb. | annual, Dec.-Feb. | annual, early March through late March | annual, early Oct. through mid Jan. |
| Foliage | | | | |
| Color | R.H.S. 143A | R.H.S. 144A | R.H.S. 143A with 59A streaking through the leaves | R.H.S. 144A |
| Size | ⅛" | Same | Same | Same |
| Shape | spike-like, with stiff, erect stems; Acerose | Same | Same | Same |
| Quantity | Abundant | Same | Same | Same |
| Bloom | | | | |
| Size | ⅛" × 1/16" | Same | 3/16" × 1/16" | ⅛" × 1/10" |
| Borne | in clusters with terminal buds | Same | Same | Same |
| Shape | Urceolate | Same | Ovoid | Urceolate |
| Color | R.H.S. 71C–71D | R.H.S. 66D | R.H.S. 70A–70B | BR.H.S. 78B–78C |
| Rate of opening: | rapid, progressive and continuous beginning at the base of the stem and progressing to the tip of the stem | Same | Same | Same |

I claim:

1. A new and distinct hybrid plant variety of the Heath family substantially as herein shown and described.

* * * * *